United States Patent [19]

Radlick

[11] 4,314,087

[45] Feb. 2, 1982

[54] METHODS OF SYNTHESIZING HEXAFLUOROISOPROPANOL FROM IMPURE MIXTURES AND SYNTHESIS OF A FLUOROMETHYL ETHER THEREFROM

[75] Inventor: Phillip C. Radlick, Irvine, Calif.

[73] Assignee: Baxter Travenol Laboratories, Inc., Deerfield, Ill.

[21] Appl. No.: 107,116

[22] Filed: Dec. 26, 1979

[51] Int. Cl.$^3$ .................... C07C 31/34; C07C 31/38
[52] U.S. Cl. .................................. 568/842; 568/400; 568/401; 568/683; 568/684
[58] Field of Search ............... 568/842, 400, 401, 683, 568/684

[56] References Cited

U.S. PATENT DOCUMENTS 3,284,347  11/1966  Hutton et al. ............... 568/842
3,702,872  11/1972  Regan ........................ 568/842

FOREIGN PATENT DOCUMENTS 722737  11/1965  Canada ....................... 568/842

OTHER PUBLICATIONS

Middleton, W. J. et al., JACS vol. 86, pp. 4948–4952, Nov. 20, 1964.

*Primary Examiner*—Paul J. Killos
*Attorney, Agent, or Firm*—Paul C. Flattery; Max D. Hensley; John P. Kirby, Jr.

[57] ABSTRACT

Hexafluoropropylene may be conventionally oxidized to form an impure mixture comprising hexafluoroacetone and residual hexafluoropropylene, which materials are separable only with difficulty. The impure mixture may be subjected to reducing conditions to hydrogenate the hexafluoroacetone to a hexafluoroisopropanol product, which product is easily separable from the hexafluoropropylene impurity, which impurity may be recycled for further oxygenation and production of the acetone. Alternatively, hexafluoroisopropanol may be conventionally made from hexachloroacetone to form an impure mixture of hexafluoroacetone and HF. When this impure mixture is hydrogenated, the resulting hexafluoroisopropanol, mixed with hydrogen fluoride, is formed. Either of these alcohol products may be reacted with hydrogen fluoride and a formaldehyde to obtain a fluoromethyl-1,1,1,3,3,3-hexafluoroisopropyl ether, which is a useful anesthetic.

12 Claims, No Drawings

METHODS OF SYNTHESIZING HEXAFLUOROISOPROPANOL FROM IMPURE MIXTURES AND SYNTHESIS OF A FLUOROMETHYL ETHER THEREFROM

BACKGROUND OF THE INVENTION

Fluoromethyl-1,1,1,3,3,3-hexafluoroisopropyl ether, as described in U.S. Pat. Nos. 3,689,571 and 3,683,092, is an anesthetic which is showing very promising results in clinical trial, being non-inflammable under conditions of use, and having advantages that appear to greatly outweigh any minor disadvantages.

For clinical use, it is necessary of course to produce the above ether material in large quantities, for example, by a synthesis technique as described in the above patents, and the abandoned original application, Ser. No. 771,365, filed Oct. 28, 1978, from which the above-cited U.S. patents claim priority.

Another currently preferred synthesis technique under consideration is the improvement as described in the patent application of Robert L. Simon et al., filed simultaneously with this present application and entitled "Method of Synthesizing Fluoromethylhexafluoroisopropyl Ether" now U.S. Pat. No. 4,250,334.

In many of these synthesis techniques, the corresponding alcohol, for example, 1,1,1,3,3,3-hexafluoroisopropanol, is a reactant. Such material is currently very expensive, largely because the various byproducts produced with the material in the presently used commercial synthesis routes and difficult to separate from the acetone precursor of the alcohol product.

In accordance with this invention, synthesis techniques are provided in which impure hexafluoroacetone mixtures may be utilized as starting material, resulting in great cost savings, since the final expensive purification steps normally utilized in the commercial hexafluoroacetone reactant are rendered unnecessary.

In one instance, the resulting alcohol product is easily separable by simple distillation from its impurities, while in another case, the original impurity is also more easily separable, but may be utilized as a reactant for the desired further step of synthesis of the hexafluoroisopropyl alcohol into the corresponding fluoromethyl ether.

DESCRIPTION OF THE INVENTION

In accordance with this invention, hexafluoroisopropanol can be synthesized from an impure mixture of hexafluoroacetone and certain impurities or byproducts resulting from economical synthesis processes for the hexafluoroacetone. The impure mixture is subjected to reducing conditions, to hydrogenate the hexafluoroacetone to a hexafluoroisopropanol product, with the impurities or byproducts being either easily separable from the hexafluoroisopropanol product, or used as reactants for the next synthesis step, which may be the synthesis of the fluoromethylhexafluoroisopropyl ether described above.

A. For example, the impure mixture utilized in this invention may comprise a mixture of hexafluoroacetone, typically about 35 to 45 percent by weight, and hexafluoropropylene in the order of about 45 to 55 percent by weight, plus small amounts of other byproduct materials. Such a reaction mixture may be manufactured in accordance with German Patent Publication No. 2,624,349, dated June 24, 1975, by means of the direct oxidation of hexafluoropropylene to hexafluoroacetone in the presence of aluminum oxide, a process commercially utilized by Daikin, a Japanese company.

In such a mixture, the hexafluoroacetone is separated only with substantial difficulty from the hexafluoropropylene. Accordingly, purified hexafluoroacetone is much more expensive than the impure mixture.

In accordance with the teachings of the German Patent Publication cited above, Example 1, the catalyst used herein may be prepared by introducing into a 28 mm.×1000 mm. pyrex glass tube in an electric furnace granular, activated aluminum oxide in a particle size between 2.4 and 4.7 mm. (alumina gel) in the amount of 51.25 grams. Dehydration may be effected by heating for one hour in a stream of nitrogen to 500° C., then allowing the temperature to drop to 200° C. Following this, an equimolar mixture of carbon tetrachloride and $CF_2ClCFCl_2$ may be fed into the top of the reaction tube at the rate of 1 gram per minute. An immediate temperature rise to 270° C. is shown in the upper portion of the aluminum oxide column, which zone of high temperature migrates slowly to the lower layer until equilibrium is reached after about 40 minutes where the aluminum oxide layer exhibits a temperature of about 10° C. higher than its original temperature.

Following this, the desired temperature may be adjusted to 250° C. while continuing to apply the halocarbon mixture to the column to possibly obtain a further hot spot moving through the column over the period of 45 minutes.

Following this, the temperature may be raised to 300° C. for 40 minutes, after which the catalyst may be removed from the furnace and cooled.

The resulting catalyst obtained in this manner may have a fluorine assay of about 9.9 percent by weight.

Fifty grams of this catalyst may be placed in a reaction tube made of Hastalloy—C, having an internal diameter of 18 mm. and a length of one meter.

A reactant gas mixture of hexafluoropropylene ($CF_3CF=CF_2$) and oxygen in the molar ratio of 1 to 0.7 may be introduced to the tube to a pressure of 5.9 bar at 170° C. The reactant gas is fed into the tube at a rate of 100 ml./min. at 25° C., arriving with a pressure of 0.99 bar and introduced until the desired pressure in the tube is achieved.

The tube is then sealed and allowed to stand at 170° C. for three hours. Following this, the gas is removed from the tube, and may be found to contain 65.6 mole percent of hexafluoropropylene and 15.9 mole percent of hexafluoroacetone, as well as certain other fluorinated compounds which are relatively easily separated from the bulk of the reaction mixture. However, the hexafluoropropylene is separated only with difficulty from the hexafluoroacetone. Accordingly, in accordance with this invention, one may subject the impure mixture to reducing conditions, to hydrogenate the hexafluoroacetone to hexafluoroisopropanol product, which is easily separated from the residual hexafluoropropylene.

A yield of 18.0 mole percent of hexafluoroacetone can be obtained in accordance with the above cited German Patent Publication when the same catalyst is brought to a temperature of 145° C. and the ratio of the hexafluoropropylene molar concentration to the oxygen molar concentration is 0.9, with the Hastalloy—C tube being filled to a pressure of 4.32 bar and the gas flow being 40 ml. per minute (See Example 8).

B. Alternatively, the impure mixture used in this invention may comprise hexafluoroacetone and hydrogen fluoride, with the hydrogen fluoride preferably being present in the range of 5 to 50 percent by weight of the impure mixture.

This impure mixture may be the product of the catalytic reaction of hydrogen fluoride and hexachloroacetone as described, for example, in the DuPont French Pat. No. 1,372,549 or the Rhone-Progil German Patent Publication No. 2,221,844.

In the product of these reactions, while the by-product hydrogen chloride is easily removed, and preferably is so removed, hydrogen fluoride is quite difficult to separate from the hexafluoroacetone, apparently because it forms a complex with the product. Accordingly, as before, purified hexafluoroacetone from these processes is much more expensive then the impure products of the reactions.

A specific example of the catalytic reaction of hydrogen fluoride and hexafluoroacetone is as described in Example 1 of the cited German Patent Publication No. 2,221,844. There, a stainless steel tube reactor is used, which may be heated from the outside with three heating elements independently operable from each other, having an internal diameter of 3.56 cm. and a length of 1.5 meters.

A chromium hydroxide gel which had been precipitated at a continuously rising temperature has been treated with anhydrous hydrogen fluoride. After the treatment and the agglomeration of the gel into granules about 5 mm. in diameter, a catalyst having a specific surface area of 186 sq. meters per gram was formed. The stainless steel tube reactor was filled, and maintained in a vertical position containing, from the bottom toward the top, a sequence of the following layers:

(1) a layer, 7 cm. high, of aluminum oxide spheres of lamellar structure, which material is relative impervious to hydrogen fluoride;

(2) a 33.5 cm. layer of the above catalyst comprising the third catalyst zone;

(3) a 7 cm. layer of more of the same type of aluminum oxide spheres;

(4) a 36.5 cm. layer of the above catalyst which serves as the second catalyst zone;

(5) a 7 cm. layer of the same type of aluminum oxide spheres;

(6) a 50 cm. layer of the chromium oxide catalyst to function as the first catalyst zone;

(7) a 6 cm. layer of the same type of aluminum oxide spheres.

The weight of catalyst used in the tube was 0.84 kg.

A gas mixture was fed through the tube, passing from the first through the third catalyst zones. The feed mixture was adjusted to include a flow of 0.94 mole per hour hexachloroacetone and 8.4 mole per hour of anhydrous hydrogen fluoride, which is a 48.8 percent stoichiometric excess of hydrogen fluoride. The pressure inside the reactor was kept constant at 1.3 bar, and the temperatures of catalyst zones 1 through 3 were maintained respectively at 236°, 265° and 310° C.

Analysis showed that the gas mixture leaving the third catalyst zone contained 96.8 percent hexafluoroacetone, based on the organic materials, plus minor amounts of other halogenated carbon compounds. Inorganic products included unused hydrogen fluoride reactant and hydrogen chloride.

While the hexafluoroacetone is relatively easily separated from the hydrogen chloride, it is only separated with substantial difficulty from the hydrogen fluoride. Accordingly, in this present invention, the mixture of hexafluoroacetone and hydrogen fluoride may be subjected to reducing conditions, to hydrogenate the hexafluoroacetone to a hexafluoroisopropanol product, specifically 1,1,1,3,3,3-hexafluoroisopropanol.

After this reducing reaction, the hexafluoroisopropanol, which has a much higher boiling point than the hexafluoroacetone, may be readily collected, being separated with ease from the residual hexafluoroacetone and the hexafluoropropylene, if present, which can outgas easily at about room temperature, for example, and may be recycled for the production of more hexafluoroacetone and alcohol.

Similarly, the product hexafluoroisopropanol is not as strongly bonded with the hydrogen fluoride as the hexafluoroacetone, so the alcohol may be easily separated from the remaining hydrogen fluoride in the reaction mixture, if desired.

However, such is preferably unnecessary, and the hydrogen fluoride can "ride" through the hydrogenation step, if desired, to serve as a reactant in the next step for synthesizing the ether product described below.

The step of hydrogenation of the hexafluoroacetone to form the alcohol may take place in presence of strong hydrogenating agents, for example, sodium borohydride in the presence of preferably methanol solvent, lithium aluminum hydride, calcium hydride, or sodium hydride, generally in the presence of an oxygen-containing, reaction-promoting solvent such as diethyl ether, methanol, isopropanol, or tetrahydrofuran.

Alternatively, the hydrogenation conditions for the hexafluoroacetone may be provided by a direct hydrogenation process in the presence of a catalyst such as Raney nickel, or various forms of platinum or palladium, such as platinum on charcoal or barium sulfate, or palladium on aluminum oxide or barium sulfate, for example as in U.S. Pat. Nos. 3,468,964 and 3,702,872.

Another hydrogenation reaction which can be used is to subject the impure mixture of hexafluoroacetone and hexafluoropropylene to aluminum triisopropoxide in the presence of a suitable solvent such as isopropyl alcohol. The reaction product is hexafluoroisopropyl alcohol and acetone, with the hexafluoropropylene being nonreactive.

Hexafluoroacetone may be converted to hexafluoroisopropyl alcohol in accordance with the Allied Chemical French Pat. No. 2,133,126 in the presence of hydrogen, in which palladium on charcoal with sodium carbonate added may be used as a catalyst. Similarly, the reaction conditions of German Patent Publication No. 2,113,551 may be used. Likewise, the teachings of U.S. Pat. No. 3,356,742 may be used to convert hexafluoroacetone in a silver-lined vessel in the presence of isopropyl alcohol into hexafluoroisopropyl alcohol.

It is preferable in the case of the acidic impure mixtures used herein to use the direct hydrogenation type of process, with a catalyst such as platinum or palladium.

Preferably, the resulting hexafluoroisopropyl alcohol product may be reacted with hydrogen fluoride and formaldehyde, preferably paraformaldehyde, in the presence of sulfuric acid and at a temperature of about 65° C. to produce fluoromethyl-1,1,1,3,3,3-hexafluoroisopropyl ether. The hexafluoroisopropanol may be added dropwise, and the product collected in a distillation column, as taught in the previously cited application of Robert L. Simon, entitled "Method of Synthesizing Fluoromethylhexafluoroisopropyl Ether."

Alternatively, other synthesis techniques may be utilized to preferably convert the alcohol product into the preferred product fluoromethyl-1,1,1,3,3,3-hexafluoroisopropyl ether.

The resulting product may be purified for use as a clinical anesthetic, having been produced in economical manner from inexpensive, impure mixtures of hexafluoroacetone, which are purified only with substantial difficulty and economic cost.

The above has been offered for illustrative purposes only, and is not intended to limit the invention of this application, which is as defined in the claims below.

That which is claimed is:

1. The method of oxidizing hexafluoropropylene to form an impure mixture comprising hexafluoroacetone and hexafluoropropylene and thereafter subjecting said impure mixture to reducing conditions to hydrogenate said hexafluoroacetone to 1,1,1-3,3,3-hexafluoroisopropanol product, whereby the product is easily separable from the hexafluoropropylene impurity.

2. The method of claim 1 in which said impure mixture is subjected to a reducing agent selected from the group consisting of sodium borohydride, lithium aluminum hydride, calcium hydride and sodium hydride, in the presence of an oxygen-containing, reaction-promoting solvent.

3. The method of claim 1 in which said impure mixture is subjected to reducing conditions by direct hydrogenation in the presence of a catalyst comprising Raney nickel.

4. The method of claim 1 in which said impure mixture is subjected to reducing conditions by direct hydrogenation in the presence of a catalyst selected from the group consisting of platinum and palladium.

5. The method of claim 1 in which said impure mixture comprises from 35 to 45 percent by weight of hexafluoroacetone and from 45 to 55 percent by weight of hexafluoropropylene.

6. The method of claim 1 in which the 1,1,1,3,3,3-hexafluoroisopropanol product is further reacted with hydrogen fluoride and a formaldehyde to yield fluoromethyl-1,1,1,3,3,3-hexafluoroisopropyl ether.

7. The method of claim 1 in which said impure mixture is reacted in the presence of aluminum isopropoxide and isopropyl alcohol to form the hexafluoroisopropanol product plus acetone.

8. The method of synthesizing 1,1,1,3,3,3-hexafluoroisopropanol from an impure mixture comprising hexafluoroacetone and hydrogen fluoride, which comprises subjecting said impure mixture to reducing conditions to hydrogenate said hexafluoroacetone to a hexafluoroisopropanol product, and thereafter further reacting said product with hydrogen fluoride and a formaldehyde to obtain a fluoromethylhexafluoroisopropyl ether.

9. The method of reacting hexachloroacetone with hydrogen fluoride to form hexafluoroacetone and HCl, with a residue of hydrogen fluoride, substantially removing said HCl to form an impure mixture of hexafluoroacetone and hydrogen fluoride, and thereafter subjecting said impure mixture to reducing conditions to hydrogenate said hexafluoroacetone to a hexafluoroisopropanol product.

10. The method of claim 9 in which said hexafluoroisopropanol product is further reacted to obtain fluoromethyl-1,1,1,3,3,3-hexafluoroisopropyl ether.

11. The method of claim 9 in which said impure mixture is subjected to reducing conditions by direct hydrogenation in the presence of a catalyst selected from the group consisting of platinum and palladium.

12. The method of claim 1 including the further step of recycling said hexafluoropropylene impurity for further oxidation and production of hexafluoroacetone.

* * * * *